(12) United States Patent
Hoth

(10) Patent No.: US 11,178,917 B2
(45) Date of Patent: Nov. 23, 2021

(54) HANDS FREE PUMPING GARMENT

(71) Applicant: BRAVADO HOLDING AG, Zug (CH)

(72) Inventor: Tara Hoth, Toronto (CA)

(73) Assignee: BRAVADO HOLDING AG, Zug (CH)

( * ) Notice: Subject to any disclaimer, the term of this patent is extended or adjusted under 35 U.S.C. 154(b) by 9 days.

(21) Appl. No.: 15/465,161

(22) Filed: Mar. 21, 2017

(65) Prior Publication Data

US 2017/0273366 A1  Sep. 28, 2017

Related U.S. Application Data

(60) Provisional application No. 62/312,454, filed on Mar. 23, 2016.

(51) Int. Cl.
| | |
|---|---|
| *A41C 3/04* | (2006.01) |
| *A41D 1/215* | (2018.01) |
| *A61M 1/06* | (2006.01) |
| *A41C 3/08* | (2006.01) |
| *A41C 3/12* | (2006.01) |

(52) U.S. Cl.
CPC ............... *A41C 3/04* (2013.01); *A41C 3/08* (2013.01); *A41C 3/12* (2013.01); *A41D 1/215* (2018.01); *A61M 1/062* (2014.02)

(58) Field of Classification Search
CPC .................................. A41C 3/04; A61M 1/062
USPC ....................................................... 450/36, 37
See application file for complete search history.

(56) References Cited

U.S. PATENT DOCUMENTS

| | | | |
|---|---|---|---|
| 321,384 | A | 6/1885 | Presley |
| 2,679,048 | A | 5/1954 | Alberts |
| D206,854 | S | 2/1967 | Sachs |
| D207,390 | S | 4/1967 | Sachs |
| 4,564,015 | A * | 1/1986 | Friedman ............. A41C 3/08 2/67 |
| 5,034,999 | A | 7/1991 | Lubbers |
| D321,273 | S | 11/1991 | Hull |
| 5,086,511 | A | 2/1992 | Kobayashi et al. |

(Continued)

FOREIGN PATENT DOCUMENTS

| | | |
|---|---|---|
| EP | 2810573 A1 | 12/2014 |
| WO | WO-96/22116 A1 | 7/1996 |
| WO | WO-2008/051484 A2 | 5/2008 |

OTHER PUBLICATIONS

U.S. Appl. No. 29/585,000, filed Nov. 18, 2016.
(Continued)

*Primary Examiner* — Alissa J Tompkins
*Assistant Examiner* — Brieanna Szafran
(74) *Attorney, Agent, or Firm* — Marshall, Gerstein & Borun LLP

(57) ABSTRACT

A nursing garment system to facilitate selective nursing and hands-free breastpumping having at least one connector configured to selectively connect a nursing bra to at least one of a hands-free breastpumping device, a nursing cover, and a breast cup of the system is disclosed. The at least one connector may include a closing device partially attached to each of the at least one of the hands-free breastpumping device, the nursing cover, and the breast cup of the system, the closing device configured to connect to a nursing bra closing device. The system may include a pumping garment having a partial figure 8 edge.

6 Claims, 7 Drawing Sheets

(56) References Cited

U.S. PATENT DOCUMENTS

| | | | |
|---|---|---|---|
| 5,514,166 A * | 5/1996 | Silver | A61M 1/064 |
| | | | 450/36 |
| 5,848,439 A | 12/1998 | Huseth et al. | |
| 6,004,186 A | 12/1999 | Penny | |
| 6,213,840 B1 | 4/2001 | Han | |
| 6,227,936 B1 | 5/2001 | Mendoza | |
| 6,346,027 B1 | 2/2002 | Merkovsky | |
| 6,440,100 B1 | 8/2002 | Prentiss | |
| 6,645,041 B2 | 11/2003 | Sarensen | |
| 6,821,185 B1 | 11/2004 | Francis | |
| 6,855,029 B2 | 2/2005 | Rothman | |
| 6,866,558 B2 | 3/2005 | Luciano et al. | |
| D505,243 S | 5/2005 | Thunstedt | |
| 6,887,217 B1 | 5/2005 | Logan | |
| 6,974,361 B2 | 12/2005 | Cravaack et al. | |
| D523,212 S | 6/2006 | Iourina | |
| 7,081,034 B1 | 7/2006 | Zoellner | |
| D571,529 S | 6/2008 | Cook | |
| 7,395,556 B2 | 7/2008 | Eraca | |
| 7,430,883 B2 | 10/2008 | Sorensen | |
| 7,611,399 B2 | 11/2009 | Brigham | |
| D625,487 S | 10/2010 | Hendrickson | |
| 7,811,248 B2 | 10/2010 | Bjorge | |
| 7,878,880 B2 | 2/2011 | Hendrickson | |
| 7,950,980 B2 * | 5/2011 | Solberg | A61M 1/062 |
| | | | 450/36 |
| D641,132 S | 7/2011 | Sharard | |
| 8,137,153 B2 | 3/2012 | Bell | |
| 8,192,247 B2 | 6/2012 | Abbaszadeh | |
| 8,226,452 B2 | 7/2012 | Hendrickson | |
| 8,323,070 B2 | 12/2012 | Abbaszadeh | |
| 8,414,353 B1 | 4/2013 | Leavell | |
| 8,469,770 B2 | 6/2013 | Alva | |
| 8,523,629 B2 | 9/2013 | Pundyk | |
| 8,668,547 B2 | 3/2014 | Boonen et al. | |
| 8,690,634 B2 | 4/2014 | Heath et al. | |
| 9,113,660 B2 | 8/2015 | Op't Hof | |
| 9,155,339 B2 | 10/2015 | Alva | |
| 9,402,425 B2 | 8/2016 | Cortese et al. | |
| D769,576 S | 10/2016 | Kawasaki | |
| 9,538,795 B2 | 1/2017 | Cobb | |
| 9,578,901 B2 | 2/2017 | Randall et al. | |
| 9,629,396 B2 | 4/2017 | Alva | |
| D799,786 S | 10/2017 | Hoth | |
| D810,397 S | 2/2018 | Beroff | |
| 9,894,942 B2 | 2/2018 | Burrell | |
| 10,231,491 B2 | 3/2019 | Akerson et al. | |
| 10,238,153 B2 | 3/2019 | Alva | |
| D854,782 S | 7/2019 | Ironi | |
| 10,405,587 B2 | 9/2019 | Cortese et al. | |
| D861,286 S | 10/2019 | Ye | |
| 10,441,002 B2 | 10/2019 | Ironi | |
| 10,463,082 B2 | 11/2019 | Boele et al. | |
| D871,718 S | 1/2020 | Pan | |
| 2003/0027491 A1 | 2/2003 | Cravaack et al. | |
| 2003/0191427 A1 | 10/2003 | Jay et al. | |
| 2003/0199224 A1 | 10/2003 | Luciano et al. | |
| 2007/0161330 A1 | 7/2007 | Whitehead et al. | |
| 2008/0034462 A1 | 2/2008 | Ekelund et al. | |
| 2008/0034463 A1 | 2/2008 | Ekelund et al. | |
| 2008/0201817 A1 | 8/2008 | Ostrander | |
| 2010/0031418 A1 | 2/2010 | Op't Hof | |
| 2010/0088800 A1 | 4/2010 | Pate-Gurule | |
| 2010/0159802 A1 | 6/2010 | Abbaszadeh | |
| 2010/0185144 A1 | 7/2010 | Bell | |
| 2011/0104985 A1 * | 5/2011 | Linder | A41C 3/0057 |
| | | | 450/58 |
| 2011/0314587 A1 | 12/2011 | Ritchie | |
| 2013/0122780 A1 | 5/2013 | McCall | |
| 2013/0232661 A1 | 9/2013 | Huntley | |
| 2013/0273809 A1 * | 10/2013 | Turk | A41C 3/0071 |
| | | | 450/36 |
| 2014/0248822 A1 | 9/2014 | Abbott et al. | |
| 2014/0273737 A1 * | 9/2014 | Cortese | A41C 3/04 |
| | | | 450/31 |
| 2014/0364036 A1 * | 12/2014 | Abbaszadeh | A61M 1/062 |
| | | | 450/36 |
| 2015/0133028 A1 | 5/2015 | Applewhite | |
| 2016/0331045 A1 | 11/2016 | Cortese et al. | |
| 2017/0042256 A1 | 2/2017 | Kawasaki | |
| 2017/0280787 A1 * | 10/2017 | Burrell | A41C 3/04 |
| 2018/0103691 A1 | 4/2018 | Alva | |
| 2019/0261698 A1 | 8/2019 | Akerson et al. | |

OTHER PUBLICATIONS

U.S. Appl. No. 62/312,454, Nursing Garment System, filed Mar. 23, 2016.

Office Action issued in Canadian Patent Application No. 2,961,802, dated Jan. 15, 2018.

International Search Report and Written Opinion, International Application No. PCT/EP2017/056641, dated Jun. 30, 2017.

Office Action issued in Canadian Application No. 2,961,802, dated Jul. 4, 2018.

Office Action, Canadian Patent Application No. 2,961,802, dated Oct. 3, 2019.

Arden All in One Nursing and Handsfree Pumping Bra, retrieved from the Internet at: <https://shop.thedairyfairy.com/arden-all-in-one-nursing-and-handsfree-pumping-bra/> Mar. 9, 2013.

* cited by examiner

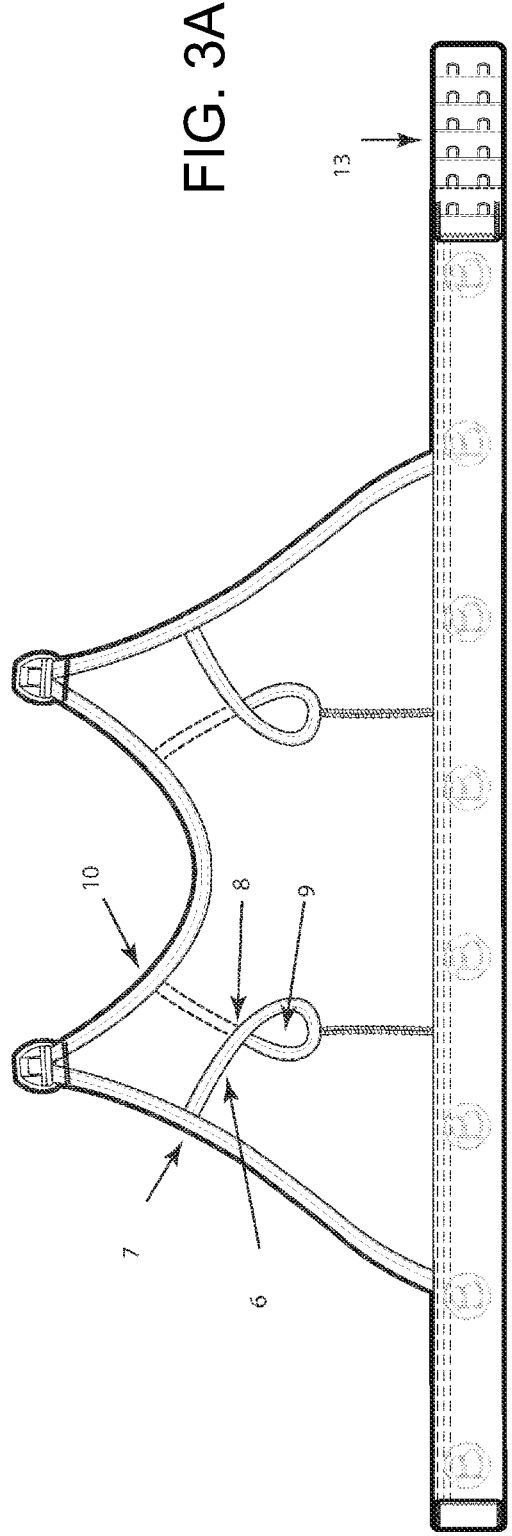

HANDS FREE PUMPING GARMENT

CROSS-REFERENCE TO RELATED APPLICATIONS

The priority benefit of U.S. Provisional Patent Application No. 62/312,454, filed Mar. 23, 2016, and entitled "Nursing Garment System," is claimed and the entire contents thereof are incorporated by reference herein.

FIELD OF THE DISCLOSURE

This disclosure relates generally to a garment for a nursing woman using a breast pump to extract milk from her breasts for storage and subsequent feeding of an infant. The garment supports the portion of a breast pump system known as a breast shield, freeing the nursing woman's hands to carry out other tasks besides holding one or two breast shields in place.

BACKGROUND

Breastfeeding of an infant provides numerous benefits to the infant and the breastfeeding woman. Breastmilk contains all of the nutrients a baby needs in the exact amounts required for optimal growth and development. Breastfed babies are healthier, having fewer middle ear infections, fewer respiratory infections, a decreased risk of developing allergies, cancer, childhood diabetes, and obesity, and being less prone to develop heart diseases, eczema, and asthma. For the breastfeeding woman, breastfeeding reduces post-delivery bleeding and chances of anaemia, aids in the uterus returning to its original size after birth, and burns up to an extra 500 calories per day.

However, not every nursing woman is able to breastfeed an infant on demand due to work schedules and other time demands. Accordingly, many nursing women use a breast pump to extract and store milk for feeding an infant. Breast pump systems routinely include a breast shield, which is a funnel-like apparatus having a conical region that is placed against the breast with the nipple in the center of the breast shield. Upon the application of negative pressure, the nipple is drawn toward, and often into, a tubular portion of the breast shield known as the nipple tunnel. The nipple tunnel of the breast shield is connected to other components of a breastmilk collection kit. This connection permits application of intermittent (i.e., cyclical) negative pressure to the interior of the breast shield, and also provides a flow path for breastmilk expressed into the nipple tunnel to be collected in a collection receptacle. The collection receptacle may be a breastmilk container having a threaded cap that can serve as a bottle for feeding an infant. A nursing woman generally has to hold the breast shield against her breast manually in order to pump milk.

Predictably, holding the breast shield in place is inconvenient and limits the tasks that the woman could otherwise accomplish while pumping. Although various brassieres and bustiers have been developed to hold the breast shield in place, such brassieres and bustiers have generally failed to adequately secure the breast shield and have required holding or frequent adjusting of the breast shield.

SUMMARY

According to an aspect of the disclosure, a nursing garment system includes at least one connector configured to selectively connect a nursing bra to at least one of a hands-free breastpumping device, a nursing cover, and a breast cup. The nursing garment system is designed to facilitate selective nursing and hands-free breastpumping. In some arrangements, the at least one connector further comprises a closing device partially attached to each of the at least one of the hands-free breastpumping device, the nursing cover, and the breast cup, the closing device configured to connect to a nursing bra closing device. The closing device may be a clip, and the nursing bra closing device may be a nursing bra clip. Accordingly, the at least one connector may comprise a clip attached to each of the at least one of the hands-free breastpumping device, the nursing cover, and the breast cup, the at least one connector further comprising a nursing bra clip, each clip of the at least one of the hands-free breastpumping device, the nursing cover, and the breast cup configured to snap fit with the nursing bra clip. In some arrangements, two connectors are provided, one on each of two straps of the nursing bra, to selectively connect the two straps of the nursing bra to at least one of a hands-free breastpumping device, a nursing cover, and a breast cup.

In some arrangements, a closure device may be disposed at the back of a bottom band of the system. More specifically, a pumping garment may include a bottom band having a fastening mechanism at a back of the pumping garment. The fastening device may include multiple points of closure to adjust the circumference of the bottom band when the pumping garment is in a closed state. The fastening mechanism may be one of snaps, Velcro, and hook and eye closures.

In some arrangements, the system may include a pumping garment having a partial figure 8 elastic edge. In some arrangements, the system may include a pumping garment having an exterior hole adapted to receive a breastshield capable of being inserted from an outside of the pumping garment. The pumping garment may include an elastic edge that starts at a side edge or top edge of the pumping garment, makes a loop at an apex, and ends at a top edge or a side edge of the pumping garment. Alternately, the pumping garment may include an elastic edge extending across a front of the pumping garment. In some arrangements, an elastic edge surrounds an exterior hole of the pumping garment and is adapted to stretch to accommodate breastshields of a variety of sizes.

In some arrangements, the nursing cover is connected to the nursing bra at a top edge of the nursing cover. The nursing cover may be secured in place only by the connection to the nursing bra. The nursing cover may be connected to two straps of the nursing bra.

BRIEF DESCRIPTION OF THE DRAWINGS

While the specification concludes with claims particularly pointing out and distinctly claiming the subject matter that is regarded as the present disclosure, it is believed that the disclosure will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. None of the drawings are necessarily to scale.

FIG. 3A illustrates an exterior view of the pumping garment depicted in FIG. 2A and 2B, the pumping garment being shown in an unfastened state.

FIG. 3B illustrates an interior view of the pumping garment depicted in FIGS. 2A, 2B, and 3A, the pumping garment being shown in an unfastened state.

DETAILED DESCRIPTION OF THE DRAWINGS

A clip in pumping garment system, or nursing garment system is hereby disclosed. The clip in pumping garment system is configured to accommodate selective attachment of a pumping garment that covers the wearer's breasts except the nipples and secures a breast shield adjacent to each breast. The clip in pumping garment system is intended to be used by a woman that is already wearing a nursing bra with suitable connectors, such as clip in cups. The hands free clip in pumping bustier is intended to be clipped into the existing nursing connectors, or clips that the woman is wearing to secure the garment at the top. The bottom of the pumping bustier is secured by an elastic band extending around the body and secured with a suitable fastening device in the back.

Figure 1A:
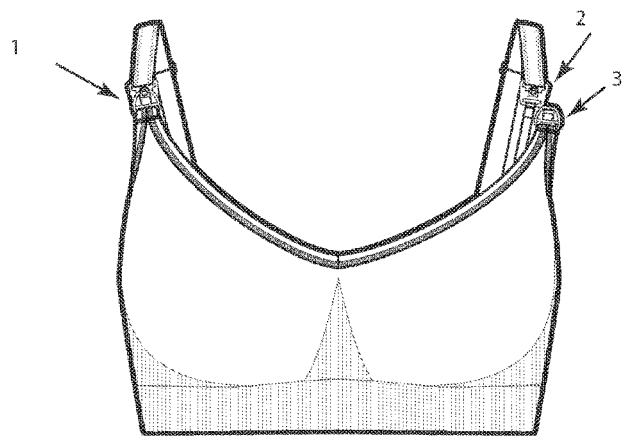
FIG. 1A illustrates a front perspective view of nursing bra in a closed and fastened state, the nursing bra having two straps, each strap having a two-piece connector.
Figure 1B:
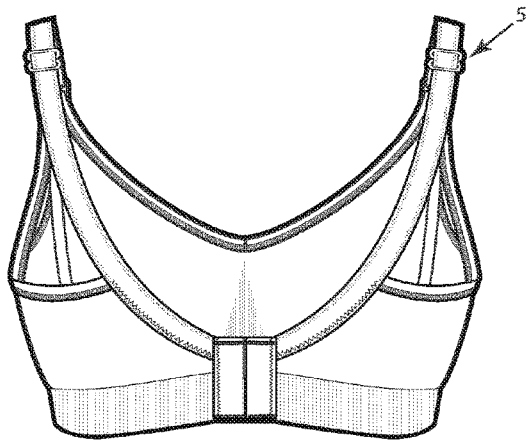
FIG. 1B illustrates a rear perspective view of the nursing bra depicted in FIG. 1A.
Figure 2A:
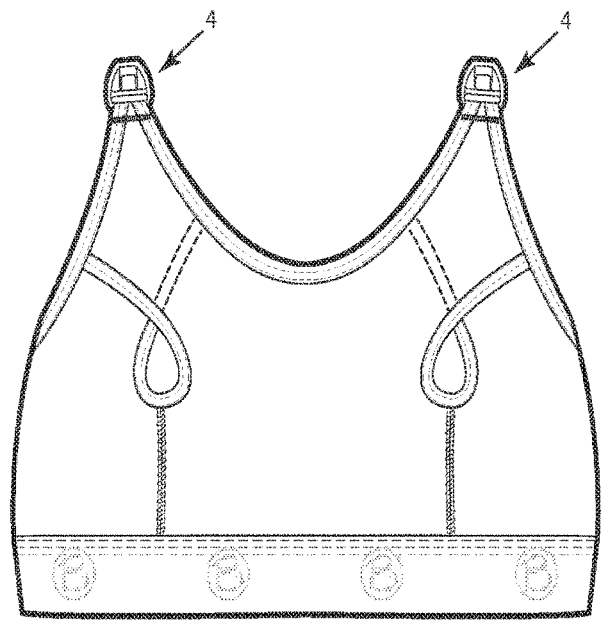
FIG. 2A illustrates a front view of a pumping garment of a hands-free breastpumping device in a fastened state, the pumping garment including a partial figure 8 elastic edge configured to support a breast shield of the hands-free breastpumping device.

The clip in pumping garment system is designed to be worn with a nursing bra that comes with a suitable connecting device, for example, a two part clip device or other suitable device that is typically placed above the nursing bra cups (1) shown in FIG. 1. One part of the two part clip device is attached to the bra strap (2) and the other part of the device is attached to the top edge of the bra cup (3). When a lactating woman disconnects this device she is able to pull the bra cup down to reveal her breast thus enabling her to breastfeed or attached her breast to a breast shield. The clip in pumping garment is designed to clip into the portion of the nursing bra clip assembly that is attached to her bra strap (2). The clip in pumping garment has a suitable connector, such as a clip (4) depicted in FIG. 2A attached to the top edge that clips into the existing nursing bra anchor (2).

Figure 5:
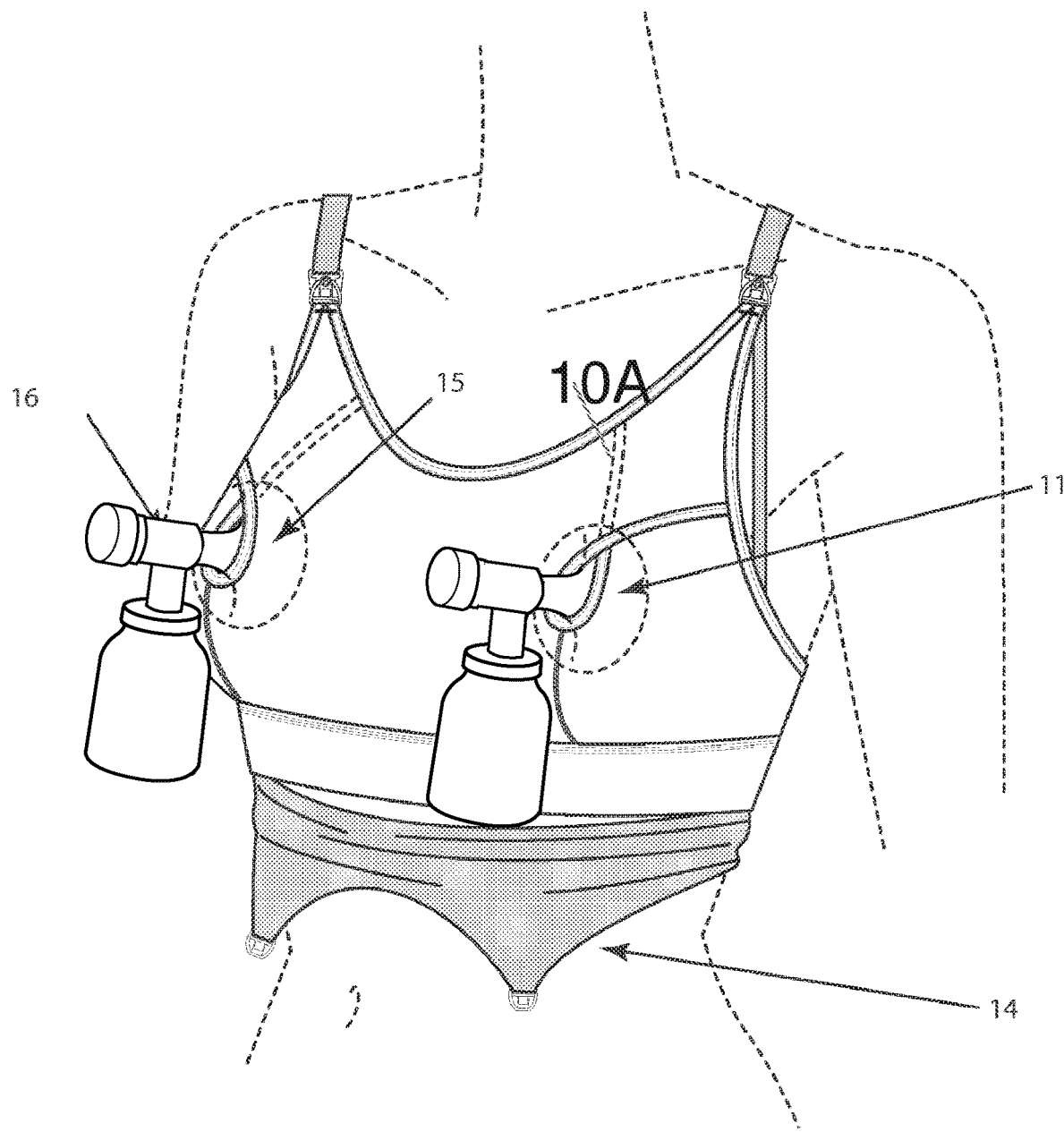
FIG. 5 illustrates a perspective view of the pumping garment depicted in FIGS. 2A, 2B, 3A, and 3B on a wearer supporting bottles and breast shields of the hands-free breastpumping device.

By utilizing the connector or anchor assembly of the existing nursing bra anchor point for the clip in pumping garment system, it provides support to the weight of the bottles as they are filled with milk. The use of the existing clip also provides the ability for the user to adjust her bra strap while wearing the hands free clip in pumping garment. This adjustment can improve the fit of the garment and ensure that the breast shield is centered on the nipple during use of the pumping bustier. The use of the existing nursing bra anchor enables the wearer to put on the hands free garment or a nursing cover without removing her existing nursing bra. This thereby simplifies the process of putting on the garment because she doesn't need to first remove her nursing bra (14) shown in FIG. 5. In addition, by not being required to remove the existing nursing bra the wearer is able to put on the hands free pumping bustier garment with far more discretion and only minimal exposure of the breast.

Figure 6:
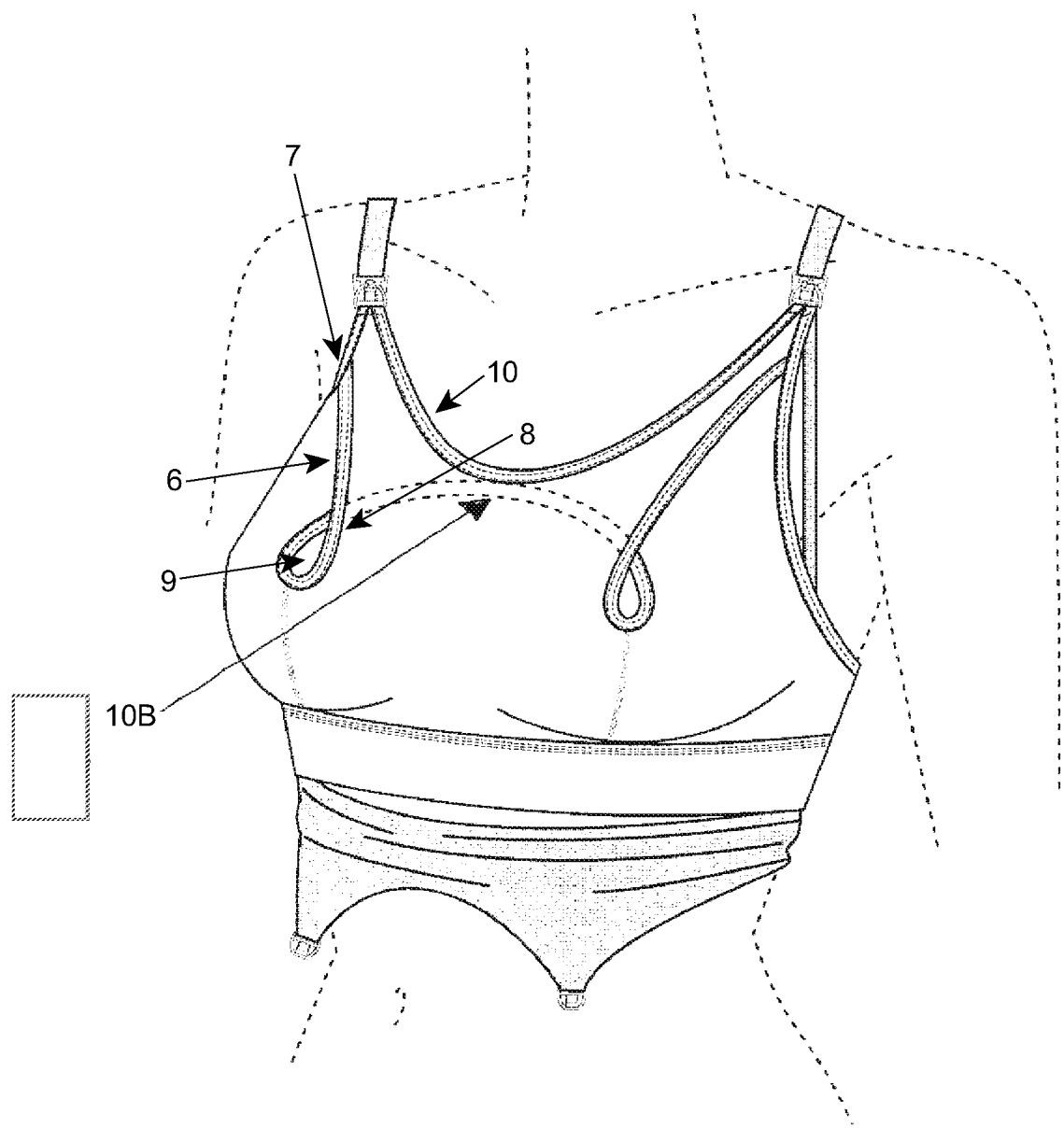
FIG. 6 illustrates a perspective view of another pumping garment of a hands-free breastpumping device in a fastened state on a wearer, the pumping garment including an elastic edge extending across the front of the pumping garment.

An exemplary embodiment of the clip in pumping garment system is made with a partial figure 8 elastic edge sewing technique specifically designed to improve the functionality of the hands free pumping garment that supports the breast shield assembly. The elastic edge (6) shown in FIG. 3A starts at the side or top edge of the garment (7) making a loop (8) at the apex (9) and ends at the top or side edge of the garment (10). The use of the partial figure 8 sewing technique delivers significantly improved functionality specifically for use of a hands free pumping garment because it enables the garment to have a small exterior hole that can accommodate the insertion of a wide variety of breast shield sizes that can be inserted from the outside of the garment (11) shown in FIG. 5. Without the figure 8 design the wearer would be required to disconnect the breast shield flange (15) from the breast shield tunnel mechanism (16) and insert the assembly from the inside of the pumping garment prior to reconnecting the breast shield assembly. Without the figure 8 design, the process as described would be repeated to remove the breast shield flange after pumping. Yet another exemplary embodiment of the clip in pumping garment is designed with the elastic edge extending across the front of the garment (10B) shown in FIG. 6.

Figure 2B:
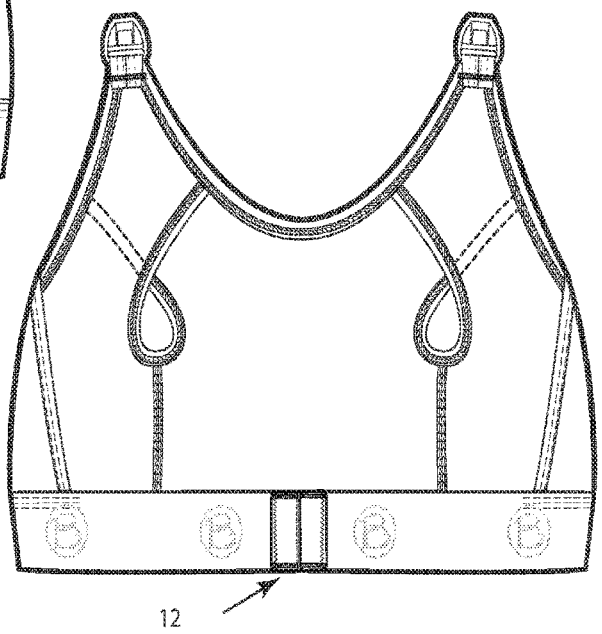
FIG. 2B illustrates a rear view of the pumping garment depicted in FIG. 2A.
Figure 4:
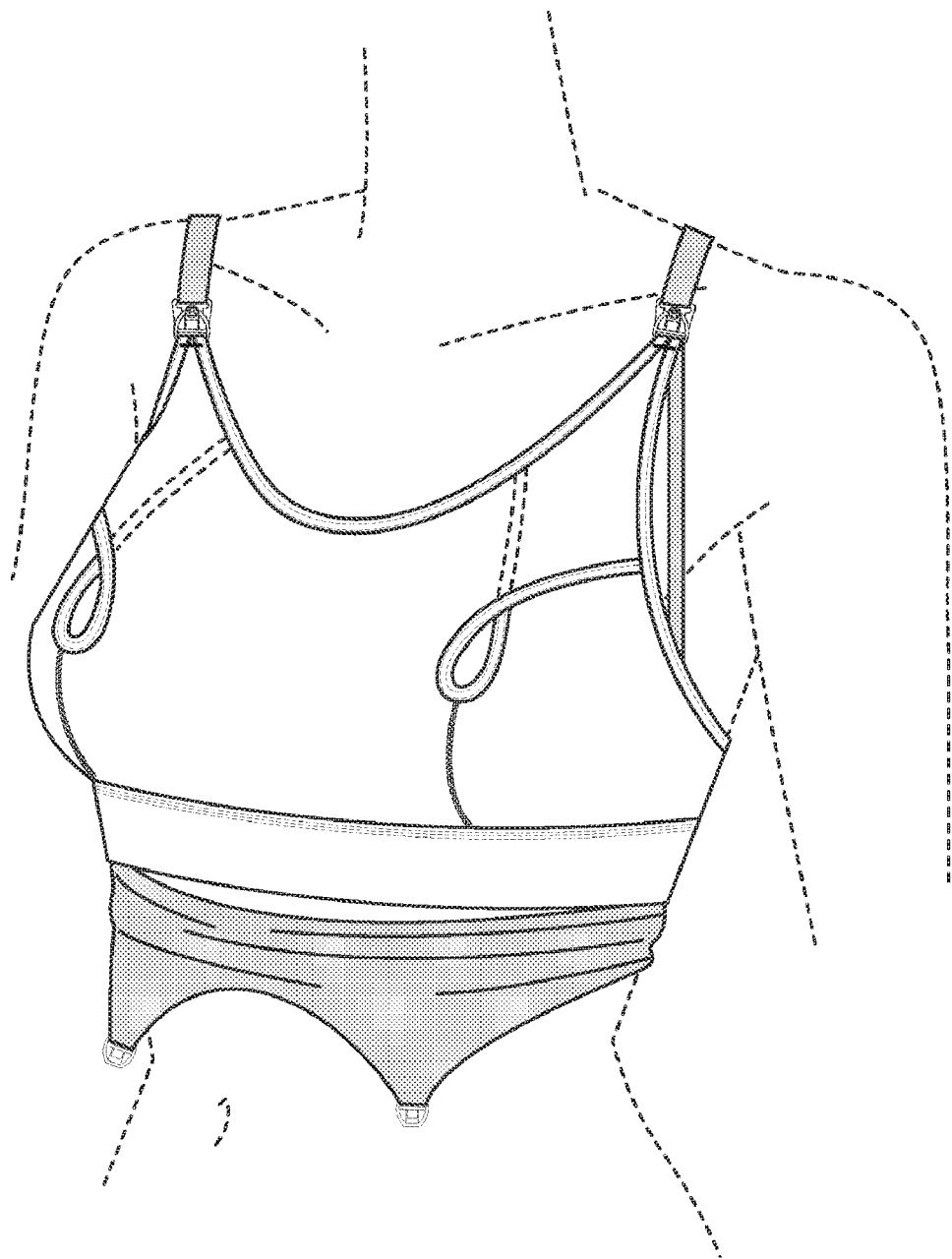
FIG. 4 illustrates a perspective view of the pumping garment depicted in FIGS. 2A, 2B, 3A, and 3B on a wearer.

The clip in pumping garment has a fastening mechanism that is designed to be closed at the back of the wearer (12) shown in FIG. 2 similar to the typical closing placement of a bra. The fastening device can be a multi row hook and eye closure or any other suitable closure, such as a snaps or Velcro, for example. The fastening device is attached to the bottom band of the clip in pumping garment. The bottom band of the pumping garment extends around the front of the garment. The fastening device can be located at the back of the body and away from the breasts and breast shields enables the bottom band to have multiple points of closure (13) shown in FIG. 3A which can adjust the circumference of the garment around the body. The fastening device at the back of the garment allows the wearer to achieve the desired tension around the body to improve the fit of the clip in pumping garment. Placement of the fastening device such as hook and eye closure allows for discrete and simple set up because the wearer can close the garment around the body without removing her nursing bra or other clothing.

Figure 7:
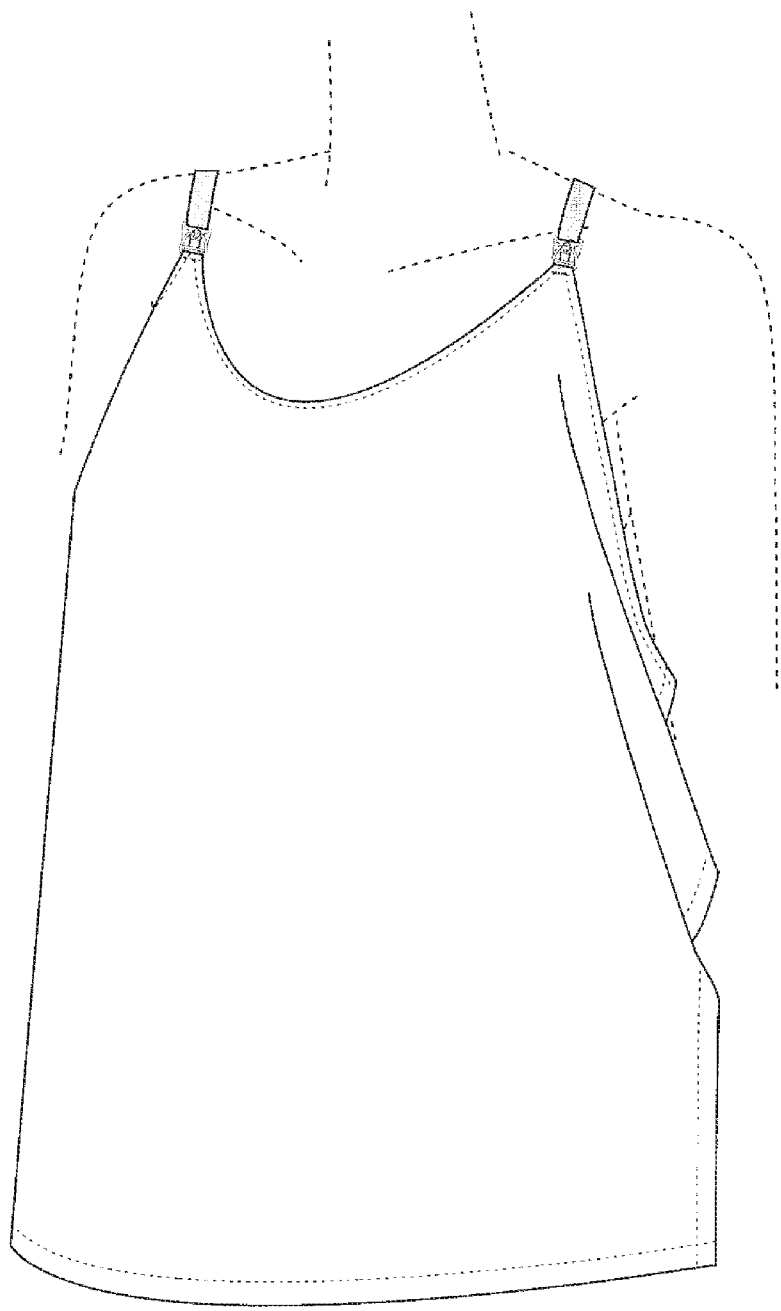
FIG. 7 illustrates a perspective view of a nursing cover connected by two-piece connectors to straps of a nursing bra on a wearer.

A nursing garment system to facilitate selective nursing and hands-free breastpumping constructed in accordance with the principles herein can include: at least one connector configured to selectively connect a nursing bra to at least one of a hands-free breastpumping device, a nursing cover shown in FIG. 7, and a breast cup.

The nursing garment system can further include: a closure device disposed at the back of a bottom band of the system, if desired.

In an embodiment, the nursing garment system can be further defined where the at least one connector includes a closing device partially attached to each of the at least one of a hands-free breastpumping device, a nursing cover, and a breast cup, the closing device configured to connect to the nursing bra closing device.

In another embodiment, the nursing garment system can be further defined where the at least one connector includes a clip attached to each of the at least one of a hands-free breastpumping device, a nursing cover, and a breast cup, the connector further including a nursing bra clip, the clip of the at least one of the hands-free breastpumping device, the nursing cover, and the breast cup configured to snap fit with the nursing bra clip.

The nursing garment system may further include two connectors, one on each of two straps of the nursing bra, to selectively connect the two straps of the nursing bra to at least one of a hands-free breastpumping device, a nursing cover, and a breast cup.

The nursing garment system may further include a pumping garment having a partial figure 8 elastic edge.

The nursing garment system may further include a pumping garment having an exterior hole adapted to receive a breastshield capable of being inserted from an outside of the pumping garment.

The nursing garment system may further include a pumping garment configured to support a breast shield assembly, the pumping garment including an elastic edge that starts at a side edge or top edge of the pumping garment, makes a loop at an apex, and ends at a top edge or a side edge of the pumping garment.

The nursing garment system may further include including a pumping garment configured to support a breast shield assembly, the pumping garment including an elastic edge extending across a front of the pumping garment.

The nursing garment system may further include a bottom band having a fastening mechanism at a back of a pumping garment, the fastening device including multiple points of closure to adjust the circumference of the bottom band when the pumping garment is in a closed state.

The nursing garment system may further include the fastening mechanism of the bottom band being one of snaps, Velcro, and hook and eye closures.

The nursing garment system may further include a pumping garment having an elastic edge that surrounds an exterior hole and is adapted to stretch to accommodate breastshields of a variety of sizes.

The nursing garment system may further include the nursing cover being secured in place only by the connection to the nursing bra.

The nursing garment system may further include the nursing cover being connected to the nursing bra at a top edge of the nursing cover.

The nursing garment system may further include the nursing cover being connected to two straps of the nursing bra.

While the present disclosure has been described with respect to certain exemplary embodiments, it will be understood that variations may be made thereto and combinations can be formed therein and varied to form sub combinations that are still within the scope of the appended claims. Additionally, while a particularly-preferred embodiment is illustrated in the drawings of the present disclosure, it will be understood that the functional features disclosed and claimed herein can be accomplished in devices that differ from these drawings, and features of the drawings are not dictated by either function or by the combinations shown.

What is claimed is:

1. A nursing garment system to facilitate selective nursing and hands-free breastpumping, comprising:

a hands-free breastpumping device that is configured to secure a breast shield adjacent to each breast;
a nursing cover; and
at least one connector configured to selectively connect a nursing bra to the hands- free breastpumping device and the nursing cover;
wherein the nursing cover and the hands-free breast pumping device, when selectively connected, are secured to the nursing bra only by one or more of the at least one connector;
wherein, in a first state, the nursing bra having a breast cup is configured to be worn by a wearer whereas the hands-free breastpumping device and the nursing cover are configured to be unworn by the wearer;
wherein, in a second state, while the nursing bra is being worn by the wearer, the breast cup is configured to be detached from a portion of the at least one connector and pulled down by the wearer to enable the wearer to breastfeed or breastpump, and either the hands-free breastpumping device or the nursing cover is configured to be put on by the wearer over the nursing bra and attached to the portion of the at least one connector in order to at least one of support bottles as they are filled with milk during breastpumping and minimize exposure of the breast of the wearer.

2. A nursing garment system to facilitate selective nursing or hands-free breastpumping, comprising:

a nursing bra having a bra strap and a breast cup configured to be pulled down to allow a wearer to breastfeed or to breastpump;
a hands-free breastpumping device that is configured to secure a breast shield adjacent to each breast;
a nursing cover; and
at least one two-part clip device comprising a first part and a plurality second parts, the first part configured to snap fit together with any one of the plurality of second parts;
wherein the first part is attached to the bra strap of the nursing bra;
wherein a first of the plurality of second parts is attached to the breast cup and a second of the plurality of second parts is attached to the hands-free breast pumping device or the nursing cover; and
wherein the hands-free breast pumping device or the nursing cover are secured to the nursing bra only by one or more of the at least one two-part clip device.

3. The nursing garment system of claim 2,
wherein the at least one two-part clip device is a first two-part clip device and a second two-part clip device;
wherein the bra strap is a first bra strap and the nursing bra further comprises a second bra strap;
wherein the first part of the first two-part clip device is attached to the first bra strap and a first part of the second two-part clip device is attached to the second bra strap;
wherein the first of the plurality of second parts of the first two-part clip device is attached to the breast cup and a first of a plurality of second parts of the second two-part clip device is also attached to the breast cup; and
wherein at least one of:
the second of the plurality of second parts of the first two-part clip device is attached to the hands-free breast pumping device and a second of the plurality of second parts of the second two-part clip device is also attached to the hands-free breast pumping device, and
the second or a third of the plurality of second parts of the first two-part clip is attached to the nursing cover and a second or a third of the plurality of second parts of the second two-part clip is also attached to the nursing cover.

4. The nursing garment system of claim 2, wherein the first of the plurality of second parts attached to the breast cup is attached to a top edge of the breast cup such that the breast cup is configured to be pulled down upon disconnection of a two-part clip device of the at least one two-part clip device.

5. The nursing garment system of claim 2, wherein the second of the plurality of second parts attached to the hands-free breast pumping device is attached to a top edge of the hands-free breast pumping device, and wherein the hands-free breast pumping device further comprises a fastening device to secure the hands-free breast pumping device around a body.

6. The nursing garment system of claim 2, wherein the second or a third of the plurality of second parts is attached to the nursing cover at a top edge of the nursing cover.

* * * * *

UNITED STATES PATENT AND TRADEMARK OFFICE
CERTIFICATE OF CORRECTION

PATENT NO. : 11,178,917 B2
APPLICATION NO. : 15/465161
DATED : November 23, 2021
INVENTOR(S) : Tara Hoth It is certified that error appears in the above-identified patent and that said Letters Patent is hereby corrected as shown below:

In the Claims

Column 6, Line 5, Claim 1, "hands- free" should be -- hands-free --.

Column 6, Line 35, Claim 2, "second" should be -- of second --.

Signed and Sealed this
Twenty-seventh Day of August, 2024

Katherine Kelly Vidal
*Director of the United States Patent and Trademark Office*